United States Patent [19]
Goldberg et al.

[11] Patent Number: 6,010,692
[45] Date of Patent: *Jan. 4, 2000

[54] METHOD AND COMPOSITION FOR PREVENTING SURGICAL ADHESIONS AND TISSUE DAMAGE

[75] Inventors: Eugene P. Goldberg, Gainesville, Fla.; James W. Burns, Holliston, Mass.

[73] Assignees: University of Florida Research Foundation, Inc., Gainesville, Fla.; Genzyme Corporation, Cambridge, Mass.

[*] Notice: This patent is subject to a terminal disclaimer.

[21] Appl. No.: 08/141,016

[22] Filed: Oct. 26, 1993

Related U.S. Application Data

[63] Continuation-in-part of application No. 08/026,125, Mar. 3, 1993, Pat. No. 5,350,573, which is a continuation of application No. 07/818,125, Jan. 8, 1992, which is a division of application No. 07/696,960, May 8, 1991, Pat. No. 5,140,016, which is a continuation of application No. 07/555,377, Jul. 19, 1990, Pat. No. 5,080,893, which is a continuation of application No. 07/199,687, May 31, 1988.

[51] Int. Cl.⁷ .................................................. A61K 31/725
[52] U.S. Cl. .................... 424/78.06; 424/423; 427/2.1
[58] Field of Search ............................. 424/78.24, 78.06, 424/78.38, 423; 427/2.1, 2.24, 2.28, 2.3

[56] References Cited

U.S. PATENT DOCUMENTS

| | | | |
|---|---|---|---|
| 4,064,564 | 12/1977 | Casey | 2/168 |
| 4,141,973 | 2/1979 | Balazs | 424/180 |
| 4,378,224 | 3/1983 | Nimni et al. | 8/94.11 |
| 4,486,416 | 12/1984 | Soll et al. | 424/180 |
| 4,585,666 | 4/1986 | Lambert | 427/2 |
| 4,589,873 | 5/1986 | Schwartz et al. | 604/265 |
| 4,651,736 | 3/1987 | Sanders | 128/305 |
| 4,657,820 | 4/1987 | Halpern et al. | 428/476.6 |
| 4,784,990 | 11/1988 | Nimrod et al. | 514/54 |
| 4,808,576 | 2/1989 | Schultz et al. | 514/54 |
| 4,819,617 | 4/1989 | Goldberg et al. | 128/897 |
| 4,840,626 | 6/1989 | Linsky et al. | 604/364 |
| 4,886,787 | 12/1989 | De Belder et al. | 514/57 |
| 4,937,254 | 6/1990 | Sheffield et al. | 514/420 |
| 4,965,253 | 10/1990 | Goldberg et al. | 514/54 |
| 5,068,225 | 11/1991 | Pennell | 514/57 |
| 5,079,236 | 1/1992 | Drizen et al. . | |
| 5,080,893 | 1/1992 | Goldberg et al. | 514/57 |
| 5,131,850 | 7/1992 | Brockbank | 435/1 |
| 5,140,016 | 8/1992 | Goldberg et al. | 514/57 |

*Primary Examiner*—Edward J. Webman
*Attorney, Agent, or Firm*—Kerkam, Stowell, Kondracki & Clarke; Dennis P. Clarke

[57] ABSTRACT

An improved method for preventing adhesions during surgery. Tissue surfaces and surgical articles involved in the surgery are coated with a solution of a hydrophilic polymeric material prior to manipulation of the tissue during surgery. The composition comprises a solution of hyaluronic acid, a salt thereof or mixtures thereof having a molecular weight of from about 50,000 to less than about 500,000 and having a concentration of from about 0.01 to about 15% by weight.

5 Claims, No Drawings

METHOD AND COMPOSITION FOR PREVENTING SURGICAL ADHESIONS AND TISSUE DAMAGE

RELATED APPLICATIONS

This application is a continuation-in-part of application Ser. No. 08/026,125 filed Mar. 3, 1993, now U.S. Pat. No. 5,350,573, which is a continuation of application Ser. No. 07/818,125 filed Jan. 8, 1992, which is a division of application Ser. No. 07/696,960 filed May 8, 1991 (now U.S. Pat. No. 5,140,016 issued Aug. 18, 1992), which is a continuation of application Ser. No. 07/555,377 filed Jul. 19, 1990 (now U.S. Pat. No. 5,080,893 issued Jan. 14, 1992), which is a continuation of application Ser. No. 07/199,687 filed May 31, 1988 (now abandoned). Related subject matter is also contained in application Ser. No. 07/750,840 filed Aug. 29, 1991, and application Ser. No. 08/141,017 filed Oct. 26, 1993. The entire contents and disclosures of each of the above-identified applications and patents are incorporated herein by reference.

BACKGROUND OF THE INVENTION

1. Field of the Invention

The present invention relates to the improvement of surgical techniques and tissue-protective surgical solutions.

2. Discussion of the Prior Art

Adhesions of the tissues involved in surgery occasioned by manipulative trauma of the tissue surfaces during the surgery and other causes such as drying and ischemic trauma constitute one of the most serious post-operative complications of surgical procedures.

Although a variety of techniques have been proposed to reduce adhesions, the problem continues to plague the art and seriously compromise even the finest and most scrupulously performed surgeries. Prior attempts to alleviate the problem and the disappointing results attendant are described by Davis et al in Surgery, Vol. 2, p. 877 (1937); Gozalez, Surgery, Vol. 26, p. 181 (1949); Hunter et al, J. Bone Joint Surg., Vol. 53A, p. 829 (1971); Ellis, Surg. Gynecol. Obst., Vol. 133, pp. 497–511 (1971); Lindsay et al, In Verdan, C. (ed.); Tendon Surgery of the Hand, London, Churchill Livingstone, pp. 35–39 (1979); Potenza, J. Bone Joint Surg., Vol. 45A, p. 1217 (1963); Verdan, J. Bone Joint Surg., Vol. 54A, p. 472 (1972); St. Onge et al, Clin. Orthop., Vol. 148, pp. 259–275 (1980); Thomas et al, Clin. Orthop., Vol. 206, pp. 281–289 (1986); Weiss et al, Bull. Hosp. Jt. Dis. Orthop. Inst., Vol. 46(1), pp. 9–15 (1986).

Goldberg et al [Arch. Surg., Vol. 115, pp. 776–780 (1980)] describe the use of certain hydrophilic polymer solutions (Povidone polyvinylpyrrolidone K-30 PVP, and dextran) to coat tissue exposed to drying and/or manipulative peritoneal trauma, as well as the surgical articles, etc., which contact the tissue before and during surgery to prevent adhesions. Although the materials and methods of Goldberg et al showed some improvement over other research studies in which hydrophilic polymer solutions were used to attempt to reduce the incidence of surgical adhesions, there still exists significant need for improvement.

A distinct disadvantage associated with the materials and methods of Goldberg et al and other prior art which has shown some benefit is the required use of highly concentrated solutions of the polymeric materials which makes practical use in surgery very difficult. Concentrated polymer solutions (greater than about 10–15%), for example, the 25% PVP and dextran solutions used by Goldberg et al, become sticky due to drying during surgery on the surfaces of tissue, surgeons' gloves, instruments, etc. This can seriously interfere with normal surgical procedures. High concentrations of PVP (K-30 molecular weight about 40,000) and dextran (molecular weight about 300,000) were required to achieve even some degree of tissue protection. Many studies prior to the report of Goldberg et al used lower concentrations of PVP, dextran or other water-soluble polymers which were even more ineffective. For example, Ellis [supra] has stated that "use of PVP was accompanied by a slightly greater incidence of adhesions" in a rat peritoneal adhesions study. He also states that because "such macromolecular solutions as plasma or dextran are known to be absorbed rapidly through functional lacunas on the under surface of the diaphragm" and "[i]t is therefore probable that any effect of PVP or any other macromolecular solution introduced into the peritoneal cavity could only be transitory." In the study by Berguist [Eur. Surg. Res., Vol. 9, p. 321 (1977)] using 10% dextran-70 (molecular weight 70,000) and 1% hyaluronic acid (molecular weight unknown), it was reported that there was "no difference between control and treated groups" for adhesions in rat and rabbit studies. Even attempts to use the relatively low molecular weight dextran-70 at very high concentrations (32%) based on suggestions of some beneficial effect in reducing genital tract adhesions in female rabbits [Neuwirth et al, Am. J. Obstet. Gynecol., Vol. 121, p. 420 (1974)] have not proven very successful. A commercial 32% (w/v) solution of dextran-70 was introduced as a hysteroscopy fluid about 1984, but recent studies have shown "no effect in reducing adhesions" using 32% dextran [Hadick et al, Military Medicine, Vol. 152, p. 144 (1987)].

Moreover, the use of such high concentrations may increase the expense of the surgical solutions and poses problems in preparing, purifying, stabilizing and storing solutions of such highly concentrated and often viscous solutions. For example, 32% dextran tends to crystallize "when subjected to temperature variations or when stored for long periods" [data sheet for commercial 32% dextran-70 solution].

Although the studies reported by Goldberg et al indicated some modest improvement in preventing adhesions using 25% PVP (molecular weight 40,000) and a slight improvement with 25% dextran (molecular weight 300,000) even using a surgical method involving coating of tissues and surgical implements before surgical manipulation, the materials and surgical solutions used were clearly impractical for clinical use in surgery.

In patent application Ser. No. 07/555,377 filed Jul. 19, 1990, now U.S. Pat. No. 5,080,893, there are described improved methods for preventing surgical adhesions in tissue by manipulation thereof during surgery comprising coating tissue surfaces involved in the surgery and/or the surfaces of surgical articles which contact the tissue surfaces during the surgery with an aqueous solution of a hydrophilic polymeric material selected from the group consisting of water-soluble, biocompatible, pharmaceutically acceptable polypeptides, polysaccharides, synthetic polymers, salts and complexes thereof and mixtures thereof prior to manipulation of the tissue during the surgery, the improvement wherein the hydrophilic polymeric material is of high molecular weight (greater than 500,000) and the solution contains from about 0.01% to about 15% by weight of the polymeric material.

The application further describes certain compositions, specifically adapted for coating the surfaces of tissues involved in surgery and preferably also the surfaces of articles which contact the tissue surfaces during the surgery to prevent surgical adhesions in the tissue by manipulation or drying thereof during surgery, consisting essentially of a pharmaceutically acceptable aqueous solution of a hydrophilic polymeric material of high molecular weight (greater than 500,000) selected from the group consisting of pharmaceutically acceptable polypeptides, polysaccharides, synthetic polymers and salts and complexes thereof and mixtures thereof. Where the polymeric material is a polysaccharide, solutions according to the invention containing from about 0.01 to less than about 1% by weight of the polysaccharide have been found to be highly advantageous. Where the polymeric material is a polypeptide or synthetic polymer, solutions according to the invention containing from about 0.01 to less than about 15% by weight thereof may be employed.

An additional embodiment of the invention described therein comprised surgical articles, surfaces of which are adapted for contacting tissue surfaces during surgery having a coating thereon formed from a composition described above.

Surgical adhesions, however, are only one of the several types of complications which arise from the damage inflicted to tissue during surgical procedures. In addition to the formation of post-operative adhesions, tissue trauma during surgery can lead to a host of other potentially serious complications during and following surgical procedures, including:

(1) excessive blood vessel damage with increased bleeding during surgery and with greater risk of post-operative hemorrhage;

(2) enhancement of (acute) post-operative inflammation with prolongation of healing and damage to adjacent healthy tissues, as well as increased potential for chronic prolonged inflammation with associated secondary complications, pain, etc.;

(3) compromised wound healing with excessive scar tissue, of particular importance in orthopedic and plastic surgery;

(4) damage to organs and tissues which can result in impaired organ function, i.e., kidneys, liver, heart, lungs, etc.;

(5) blood vessel damage which can reduce blood supply with partial ischemia of muscle tissues and organs, leading to compromised function of muscle and vital organs, which is a life-threatening situation for heart muscle damage; and (6) increased susceptibility to acute and chronic infections due to preferential adherence and growth of pathogens on damaged tissue sites (post-operative staph and pseudomonas infections) with increased difficulty in treatment, slower recovery and greater chance of life-threatening systemic sepsis.

All of the above tissue damage related complications can result in longer hospitalization, patient discomfort, greater risk of morbidity and mortality, greater incidence of re-hospitalization and corrective surgery with associated patient risks, and higher health care costs.

Desiccation and abrasion tissue damage during surgery can lead to a variety of pathological surgical and post-operative complications. Damage due to desiccation and abrasion of the ovaries often results in formation of a thin fibrous membrane over the surface of the organ. Often this membrane is difficult to see with the unaided eye, yet it can act as a physical barrier to prevent transport of an egg to the Fallopian tube, thus preventing fertilization.

Prosthetic devices and implants such as heart valves, ventricular assists, vascular grafts, ligaments, tendons, corneas, skin grafts, muscle grafts and the like which are derived entirely or in part from animal or human tissue or organs are subjected to handling and manipulation in the normal course of harvesting, processing, manufacturing, shipping and storage of prostheses. Some specific examples of such bioprostheses include, but are not limited to, porcine heart valves, fetal tissue derived vascular grafts (e.g., from umbilical tissue), fetal neurological tissue, electrically activated muscle blood pumps (e.g., ventricular assist devices), and the like. The manipulation of these tissue derived bioprostheses and organ transplants can damage tissues, e.g., by desiccation or abrasive trauma, and thereby adversely affect in vivo biophysical or biochemical properties and reduce the safety and efficacy of the bioprosthesis or organ transplant. Organ and tissue transplants such as hearts, lungs, kidneys, livers, corneas, tendons and the like can be similarly damaged by the normal manipulation that occurs with harvesting, storing, preparing, processing, shipping and implanting organs, tissues or composite bioprostheses into recipient patients.

It is an object of the present invention to provide another improved method of preventing surgical adhesions during surgery.

It is another object of the present invention to provide improved compositions and methods for protecting tissue and preventing tissue damage in surgery.

It is an additional object of the present invention to provide improved methods and compositions for protecting human and animal derived tissues and organs during the manipulations that occur during harvesting, processing, storing, shipping and implantation thereof from trauma and damage which can result in impaired organ or tissue function or induce undesirable biological behavior.

Finally, it is a further object of the present invention to provide improved compositions and methods for protecting those parts of bioprostheses derived from animal or human tissues or organs from trauma and damage during the harvesting thereof and the manufacture, processing, storing, manipulation, shipping and implantation of the bioprosthesis, which trauma or damage could result in impaired bioprosthesis function or induce undesirable biological behavior.

SUMMARY OF THE INVENTION

An embodiment of the present invention comprises a method of preventing post-operative surgical adhesions of tissue and protecting tissue and preventing tissue damage in surgery comprising providing the tissue surfaces involved in the surgery with a wet coating of a physiologically acceptable aqueous solution of a hydrophilic polymeric material prior to manipulation of the tissue during the surgery, wherein:

a) the polymer material is hyaluronic acid having a molecular weight from about 50,000 to less than about 500,000, a pharmaceutically acceptable salt thereof, complex or mixtures thereof; and b) the concentration of the aqueous solution of the polymeric material is in the range of from about 0.01% to about 15% by weight, the molecular weight and concentration having values such that the aqueous solution is capable of providing wet coatings on the tissue.

Another embodiment of the present invention is a method of protecting tissue and preventing tissue damage in surgery comprising providing surfaces involved in the surgery with a wet coating of a physiologically acceptable aqueous solution of a hydrophilic, polymer material prior to manipulation of the tissue during surgery, wherein:

a) the polymer material is hyaluronic acid having a molecular weight from about 50,000 to less than about 500,000, a pharmaceutically acceptable salt thereof, complex or mixtures thereof; and b) the concentration of the aqueous solution of the polymeric material is in the range of from about 0.01% to about 15% by weight, the molecular weight and concentration having values such that the aqueous solution is capable of providing wet coatings on the tissue.

Yet another embodiment of the present invention comprises a surgical article, surfaces of which are adapted for contacting tissue surfaces during surgery having a coating thereon formed from one of the compositions described above.

A further embodiment of the present invention relates to a method of protecting from damage tissues or organs during the harvesting thereof from animals or humans, the manufacture therefrom of bioprostheses and the subsequent manipulations and implantations of the bioprostheses in animals or humans, comprising providing the tissue or organ surfaces with a wet coating of a physiologically acceptable aqueous solution of a hydrophilic, polymer material prior to and during the harvesting, manufacture of bioprostheses, manipulations and implantations thereof, wherein:

a) the polymer material is hyaluronic acid having a molecular weight from about 50,000 to less than about 500,000, a pharmaceutically acceptable salt thereof, complex or mixtures thereof; and b) the concentration of the aqueous solution of the polymeric material is in the range of from about 0.01% to about 15% by weight, the molecular weight and concentration having values such that the aqueous solution is capable of providing wet coatings on the tissue.

DETAILED DESCRIPTION OF THE INVENTION

The present invention is predicated on the discovery that surgical adhesions and damage to tissue from surgical procedures may be prevented to a far greater extent than previously achieved by ensuring pre-coating of the involved tissues prior to the surgical manipulation thereof with the above-described solutions.

In addition to the compositions described in the above-noted patent application, it has since unexpectedly been discovered that solutions of hyaluronic acid having molecular weights less than that designated in said prior application, but of sufficient concentration to provide the appropriate viscosities, are also useful for the prevention of surgical adhesions and surgical damage to tissue.

Viscosity of the polymeric solutions is determined by the molecular weight and concentration of the polymer in the solution. This relationship is empirically described by the equation $\eta$ MC [Ferry, "Viscoelastic Properties of Polymers," pages 541–542, J. Wiley & Sons, New York (1970)]. Accordingly, as either or both HA molecular weight and concentration increase, the viscosity of the solution likewise increases. It has been discovered that the ability of the hyaluronic acid solutions to prevent tissue damage and thereby reduce adhesion formation is related to the viscosity of the solution, not just molecular weight or concentration. Thus, low molecular weight polymer at the appropriate concentration provides sufficient viscosity to protect tissue from surgical damage and, therefore, adhesion formation. Thus, for example, a solution of lower molecular weight of HA of 245,000 D with a concentration of 2.8% will have a viscosity equivalent to a solution of 1.75 million D molecular weight HA at 0.38% which is 180–200 cps (see Table 1).

The novel compositions of the invention unobviously reduce the incidence of surgical adhesions and damage to tissue from surgical procedures to a far greater degree than would be expected from a reading of the extensive literature in this field.

It has been found, as demonstrated hereinbelow, that combined use of the lower molecular weight hydrophilic polymer solutions in the high concentration range described herein results in an unexpected significant decrease in the risk of surgical adhesions and tissue damage.

The unexpected benefit of using the polymer compositions of this invention with pre-coating of the involved tissue has been clearly shown to give far better results than post-operative or post-tissue manipulative treatment or coating.

Furthermore, the surprisingly advantageous tissue-protective, adhesions preventive properties of the compositions of this invention have been demonstrated when used to coat tissue prior to surgical manipulation even when conventional irrigating solutions are subsequently used during surgery.

For purposes of the present invention, the following definitions are applicable herein.

"Surfaces" refers to the surfaces of all tissue involved in and subject to manipulation by a foreign object during surgery or exposed to traumatic drying in the surgical field, as well as the surfaces of all surgical articles used in surgery and which may contact the involved tissue.

"Involved tissue surfaces" refers to all tissue involved in and subject to manipulation by a foreign object during surgery, exposed to traumatic drying in the surgical field or exposed to gases such as $CO_2$ during endoscopic procedures.

"Surgical articles" refers to all instruments, devices, accessories, swabs, sponges, gauzes, gloves, sutures, etc., used in surgery and which may contact the involved tissue.

"Surgery" refers to all invasive surgical techniques including endoscopic procedures which expose tissue subject to surgical adhesions.

"Manipulation" refers to all contact with involved tissue which causes surgical adhesions or tissue damage.

"Surgical adhesions" refers to the collagenous connective tissue which develops post-operatively after manipulative trauma to the involved tissue. Also defined by this term are adhesions produced from involved tissue due to drying and/or ischemic trauma during the surgical procedure.

The term "tissue damage" refers to an insult to the surface of hard and soft tissues and organs that results in a temporary or permanent effect on the physical, physiological or biochemical state of the tissue such as eliciting a wound healing or inflammatory response, discoloration due to desiccation or abrasive trauma, visual or microscopic damage to epithelial or endothelial surfaces, changes in tissue mechanical properties, i.e., embrittlement due to drying and changes in metabolic function of surface cell layers, e.g., enzyme function.

"Coating formed from the aqueous composition" refers to the "wet" coatings formed on the coated surfaces using the aqueous composition, as well as coatings formed from the aqueous composition which are dried and may be subsequently re-wetted to produce the wet coating.

The term "prosthesis" refers to a device for replacing a part of the body of a human or animal.

The term "bioprosthesis" refers to a prosthesis composed at least in part from human or animal derived tissues or organs.

In general, there is extensive literature on attempts to use various hydrophilic polymer solutions to prevent surgical adhesions by applying such solutions to the tissue surfaces in the surgical field following manipulative procedures and tissue trauma and just prior to wound closure. The concept guiding such studies has been that the viscous polymer solutions might afford a protective barrier to bridging of the traumatized tissues by collagenous connective tissue (adhesions). Polyvinylpyrrolidone (PVP), carboxymethylcellulose (CMC), dextran (dex) and hyaluronic acid (HA) have all been investigated, but no clinically practical results have been achieved.

The present invention is predicated on the discovery that a major improvement in the prevention of adhesions and tissue damage is surprisingly achieved with aqueous hydrophilic polymer solutions of molecular weight and concentration to provide sufficient viscosity using a method of tissue protection involving the application of the polymer solution to the tissue before surgical manipulative procedures are initiated. This combination of materials and method of use results in uniquely successful tissue protection and prevention of surgical adhesions and overcomes the drawbacks of the prior art where either (1) the polymers used (i.e., PVP or dextran) have been of molecular weights less than 500,000 necessitating high concentrations (greater than 20%) to have sufficient viscosity to provide any beneficial effect and, therefore, exhibiting difficult physical handling properties during surgery and/or (2) the solutions have been used by a method involving coating of tissues at the conclusion of surgery, thus not affording the tissue protection during surgery which is provided by the method of this invention. Thus, by the combined use of (a) more dilute aqueous hydrophilic polymer solutions made possible with polymers having molecular weights greater than 50,000 and concentrations to provide sufficient viscosity to protect tissue surfaces from damage during surgery and (b) a method of use wherein the solution is used as a tissue protective coating at the beginning of surgery, it has been discovered that a major improvement in preventing surgical adhesions, which is clinically practical, is achieved.

This invention is predicated on the use of the viscous polymer solutions described herein.

Unexpectedly, we have discovered that dilute HA solutions of HA with molecular weights of from about 50,000 to less than about 500,000 are effective at concentrations of up to 3–5% by weight and apparent viscosity of 5 to 200 cps or greater when used for surgical adhesions prevention and tissue protection by our method of application. Such HA solutions, therefore, represent efficient materials for the method of this invention because of the excellent biocompatibility, favorable non-Newtonian rheology and tissue coating by dilute solutions, practical cost for general surgical applications which may require 1–2 liters of the dilute solutions, and adhesion prevention qualities when combined with the method of use according to the invention.

Virtually all types of surgery in which post-operative adhesions represent a significant complication (e.g., peritoneal, pericardial, obstetric, laparoscopic, endoscopic, gynecological, neurological, ENT, dental, arthroscopic, orthopedic, plastic, reconstructive, prosthetic, muscle or tendon) are susceptible to modification and improvement according to the present invention. Important examples include abdominal, thoracic, cardiovascular, ob/gyn, and neurosurgical procedures, all of which are fraught with potentially severe post-operative complications which may be attributed to surgical trauma. In the case of cardiac surgery involving transplants, vascular repair and by-passes, valve replacements, etc., reoperations continue to increase every year with repeat coronary artery surgery comprising the majority of such reoperations. Post-operative pericardial adhesions from initial surgery are common and subject patients undergoing repeat cardiac surgery to substantial risks. Potential injury to the heart, great vessels and extra-cardiac grafts during resternotomy, as well as prolonged operative time, increase morbidity and mortality. Resternotomy is associated with as much as a 6% incidence of major vascular injury and a more than 35% mortality has been reported for patients experiencing major hemorrhage during resternotomy. A 50% mortality has been reported for associated injuries to aortocoronary grafts. Pediatric cardiac surgery is also associated with a very high incidence of reoperations. In view of the marked increase in cardiac surgery and reoperations and the potentially serious complications related to pericardial adhesions, prevention of such adhesions represents a major health care need. The significant reduction in pericardial adhesions as well as tissue damage made possible by the materials and method of this invention is illustrated in the following examples.

Peritoneal adhesions represent another major health care problem with potentially serious post-operative complications associated with all types of abdominal surgery, with a reported incidence of 50–90% for laparotomies. As indicated in the following examples, a dramatic reduction in abdominal adhesions is made possible and clinically practical by the use of the materials and method of this invention.

The hydrophilic polymer material may be dissolved in any suitable aqueous solution conventionally employed in surgery, e.g., Ringer's lactate, normal saline or any other iso-osmolar physiological medium.

EXAMPLES

It has been previously disclosed that sodium hyaluronate (HA) solutions showed significant reduction of post-operative adhesions formation when the HA solutions were used to pre-coat tissues and thereby reduce surgical trauma [Goldberg et al, Transactions of the 17th Annual Meeting of the Society for Biomaterials, p. 252 (1991)]. An additional study verified these results and also demonstrated that HA solutions were more effective at higher concentrations and viscosities than were solutions of lower HA concentrations and viscosities. Results from this study are included herein and are referred to as Study 3.

Two further studies were performed to elucidate the relative effects of HA molecular weight, concentration and solution viscosity. Study 1 determined the effects of HA molecular weight and concentration on adhesion reduction when the viscosity of the solutions was held constant (180–200 cps). Study 2 determined the effects of solution viscosity and molecular weight on adhesion reduction when HA concentration was constant (0.4%).

Animal Model

A rat cecal abrasion model, employing a constant force auto-abrader, was used to evaluate HA solutions over a range of viscosities and molecular weights. The auto-abrasion method was developed to cause reproducible and controlled tissue damage and for reproducibly inducing adhesion formation. The device utilizes a rotating spline shaft which is free to move vertically. The abrasion force is provided by the weight of the shaft and, since the shaft is free to move, slight hand movement will not change the abrading force. The shaft is connected to a battery-driven motor which turns the shaft at a constant rate. The abrading surface used in all experiments was Type VII surgical gauze (1.77 cm² surface area) secured to the end of the shaft. The cecum was secured during abrasion in a Teflon device containing a hole large enough to accommodate the abrading surface. The abrasion parameters were standardized to provide reproducible results. Abrasion force was 70 gm, the shaft was rotated for 60 revolutions at 130 rpm for each abrasion site, and the cecum of each animal was abraded proximally and distally on the anterior and posterior sides of the cecum for a total of four abrasion sites.

All experiments were performed using a random/blind protocol. Treatment solutions and animals were fully randomized so that animal groups were not done sequentially.

Experimental Protocol

Sprague Dawley female (200–250 gm) rats were anesthetized by an intramuscular injection of ketamine (100 mg/kg body weight) and xylazine (10 mg/kg body weight). The peritoneum of each animal was surgically exposed via a 4–5 cm mid-abdominal incision. Two ml of solution were used to coat the abdominal organs and the cecum was maneuvered out of the abdominal cavity with cotton swabs precoated with the test solution. The cecum was coated with an additional 2 ml of solution (1.0 ml on the anterior cecum and 1.0 ml on the posterior cecum) and abraded at four sites. The cecum was replaced in the abdominal cavity after abrasion, and the incision was closed. One week following surgery, the animals were sacrificed by $CO_2$ asphyxiation, the peritoneal cavity was accessed via a left paramedian incision and adhesions were graded according to the 0–4 scale (Table 1).

Study Groups

For Study 1, HA solutions with varying molecular weights were formulated to a constant viscosity of approximately 180–200 cps. The concentration of HA was varied from 2.83 wt. % at 245,000 D HA to 0.26 wt. % for 2.27 million D HA.

In Study 2, the effects of solution viscosity and HA molecular weight on adhesion reduction was investigated. The solutions were formulated with HA of varying molecular weights to a constant concentration of 0.4 wt. % with a viscosity range of 1 to 1,600 cps (see Tables 1 and 2).

In Study 3, the effects of HA solution viscosity on adhesion reduction was determined. HA solutions were formulated with HA of constant molecular weight at HA concentrations of 0.1% to 0.4%. The viscosities of these solutions ranged from 5 to 180 cps.

All test solutions were formulated aseptically in phosphate buffered saline solution (PBS) adjusted to pH 7.0. PBS control groups were included in Studies 1 and 2.

Viscosities of the HA solutions were measured at 25° C. with a Brookfield cone and plate viscometer model LVTDV II with a CP 40 cone. All HA concentrations and molecular weights were determined by size exclusion chromatography coupled with multiple angle light scattering analysis of the test solutions [Yu et al, in Zadisch, M. and Bose, A. (eds.), Harnessing Biotechnology For the 21st Century, Washington, D.C., Amer. Chem. Soc., pp. 80–84 (1992)].

Statistical Analysis

The percent of animals with significant adhesions (grade 2 or higher; See Table 1 for adhesion scoring scale) were compared among the different treatment groups by Chi-square analysis. The data reported and analyzed refers to the number of animals with cecal adhesion scores of 2 or higher.

The results from Study 1, which evaluated the effects of HA molecular weight on adhesion reduction at constant viscosity, are presented in Table 2. HA molecular weight varied from 245,000 D to 2.27 million D. All animal groups receiving HA solutions had significantly fewer adhesions ($p<0.005$) of grade 2 or higher compared to the PBS group. Also noted in Table 2 is the average incidence of cecal adhesions, i.e., the total number of cecal adhesions divided by the number of animals in the group, which was also significantly reduced in all groups receiving HA solutions as compared to the PBS group. Comparison of HA treatment groups by Chi-square analysis failed to demonstrate statistical differences between the groups ($p>0.05$). Based on this data, there was no apparent effect of HA molecular weight on adhesion reduction when solution viscosity was held constant. From this data, and from Study 3 (Table 4) which showed that adhesion reduction was related to solution viscosity or HA concentration, either HA concentration or solution viscosity could be responsible for the ability of HA solutions to protect tissues from surgical trauma and reduce adhesion formation.

Therefore, for Study 2, the HA concentration of the HA solutions tested was maintained at 0.4 wt. % and the HA molecular weight (and, therefore, viscosity of the solutions) was varied from 300,000 D to 2.30 million D. Results of Study 2 are presented in Table 3. As in Study 1, the HA group had significantly fewer adhesions of grade 2 or higher than the PBS group ($p<0.005$). This study indicates that, in the range of HA molecular weight and concentration of this invention, as the viscosity of HA solutions increases, the adhesions prevention and tissue protection efficacy increase as well.

In Study 3 (see Table 4), the molecular weight of HA in each solution was 1.5 million D and the concentrations tested were 0.1 wt. %, 0.25 wt. % and 0.4 wt. %. Each HA solution reduced adhesions compared to the PBS or no coating groups. As solution concentration and, therefore, viscosity increased, the ability of the solutions to reduce adhesions formation also increased.

Hydrophilic polymeric solutions have been extensively studied for reducing post-operative adhesion formation. These solutions generally were usually somewhat viscous, were applied in large volume to the surgical field at the end of surgery (therefore, after tissue damage had occurred) and were relatively ineffective. On the other hand, the HA solutions of this invention act to reduce adhesion formation by pre-coating surgical tissues, thus providing a visco-protective barrier during surgery which reduces tissue trauma and adhesion formation.

On the basis of Studies 1, 2 and 3, the relative contributions of HA concentrations, molecular weight and solution viscosity on the ability of HA solutions to reduce surgical adhesion formation can be discerned. In Study 1, when the HA viscosity was maintained at 180–200 cps, neither HA concentration nor molecular weight affected adhesion reduction, thus indicating that at least one of these variables did not affect adhesion reduction. Study 2 showed that for a constant HA concentration, the viscosity or molecular weight of HA affected adhesion reduction. The results from these two studies with those of Study 3 (showing a dose response for HA concentration or viscosity) indicates that viscosity of HA solutions is the most important factor in determining the tissue protective and adhesion prevention efficacy of HA solutions. Therefore, HA with molecular weights less than 500,000 are effective if used at concentrations sufficient to afford suitable solution viscosity (i.e., >5–10 cps).

TABLE 1

Scale for Evaluation of Cecal Adhesions

0 = No adhesions
1 = Filmy adhesion
2 = Mild adhesion with freely dissectable plane
3 = Moderate adhesion with difficult dissection of plane
4 = Dense adhesion with non-dissectable plane

TABLE 2

Study 1:
Effect of HA Molecular Weight
On Adhesion Prevention

| Group | HA Concentration % (w/w) | % Animals With At Least One Adhesion ≧ 2 | Average Incidence of Cecal Adhesions |
|---|---|---|---|
| PBS | N/A | 85 (17/20) | 1.95 ± 1.0 |
| 245,000 | 2.83 | 30 (6/20)[1] | 0.85 ± 0.88 |
| 390,000 | 1.89 | 25 (5/20)[1] | 0.75 ± 0.85 |
| 940,000 | 0.80 | 20 (4/20)[1] | 0.55 ± 0.69 |
| 1,750,000 | 0.38 | 35 (7/20)[1] | 0.80 ± 0.95 |
| 2,270,000 | 0.26 | 10 (2/20)[1] | 0.45 ± 0.76 |

[1]Significantly different than PBS group as determined by Chi-square analysis ($p < 0.005$). All other groups are not statistically different ($p < 0.05$) by Chi-square analysis.

Each solution was formulated to have the approximate apparent viscosity (180–200 cps) of a 0.4 wt. % solution of approximately 1.5 to 1.8 million molecular weight HA.

TABLE 3

Study 2:
Effect of HA Solution Viscosity
On Adhesion Prevention
(HA Concentration = 0.4% w/w)

| Group n = 20 animals | Viscosity (cps) | HA Mw (× 10⁵D) | % Animals With Adhesions ≧ 2 | Average Incidence of Adhesions |
|---|---|---|---|---|
| I | 1 (PBS) | N/A | 74 (14/19) | 1.68 ± 1.11 |
| II | 4 | 3.0 | 40 (8/20) | 1.25 ± 0.97 |
| III | 11 | 5.5 | 47 (9/19) | 1.05 ± 1.03 |
| IV | 29 | 9.5 | 30 (6/20) | 0.90 ± 0.85 |
| V | 182 | 14.5 | 15 (3/20) | 0.40 ± 0.60 |
| VI | 1,580 | 23.0 | 10 (2/20) | 0.15 ± 0.37 |

Groups II, III, IV, V and VI are significantly different than Group I (Chi-square analysis $p < 0.005$).
Group VI is significantly different than Groups II and III (Chi-square analysis $p < 0.05$).
Group V is significantly different than Group III (Chi-square analysis $p < 0.005$).

TABLE 4

Study 3:
Effect of HA Concentration (wt. %) and
HA Solution Viscosity on Adhesion Prevention

| Test Group | % Animals with Adhesions ≧ 2 |
|---|---|
| No Coating | 92 (23/25) |
| PBS | 88 (22/25) |
| 0.1% HA | 36[1,2] (9/25) |
| 0.25% HA | 24[1,2] (6/25) |
| 0.4% HA | 12[1,2,3] (3/25) |

[1]Significantly different than PBS group for $p < 0.005$.
[2]Significantly different than no coating group for $p < 0.005$.
[3]Significantly different than 0.1% HA group for $p < 0.005$.

We claim:

1. A method of preventing post-operative surgical adhesions of tissue and protecting tissue and preventing tissue damage in surgery comprising providing said tissue surfaces involved in said surgery with a wet coating of a physiologically acceptable aqueous solution of a hydrophilic polymeric material prior to manipulation of said tissue during said surgery, wherein:

a) said polymeric material is hyaluronic acid having a molecular weight from about 50,000 to less than about 500,000, a pharmaceutically acceptable salt thereof, complex thereof or mixtures thereof; and b) the concentration in said aqueous solution of said polymeric material is in the range of from about 0.01% to about 15% by weight; said molecular weight and concentration having values such that said aqueous solution is capable of providing wet coatings on said tissue.

2. The method of claim 1 wherein said surgery is peritoneal, pericardial, abdominal, obstetric, laparoscopic, endoscopic, gynecological, neurosurgical, ENT, dental, arthroscopic, orthopedic, plastic, reconstructive, prosthetic, muscle or tendon.

3. The method of claim 1 wherein said involved surfaces coated with said solution of polymeric material comprise tissue or surgical article surfaces or both.

4. A method of protecting from damage tissues or organs during harvesting thereof from animals or humans, manufacture therefrom of bioprostheses and subsequent manipulations and implantations of said bioprostheses in animals or humans, comprising providing said tissue or organ surfaces with a wet coating of a physiologically acceptable aqueous solution of a hydrophilic, polymeric material prior to and during said harvesting, manufacture of bioprostheses, manipulations and implantations thereof, wherein:

(a) said polymeric material is hyaluronic acid having a molecular weight from about 50,000 to less than about 500,000, a pharmaceutically acceptable salt thereof, complex thereof or mixtures thereof; and (b) the concentration in said aqueous solution of said polymeric material is in the range of from about 0.01% to about 15% by weight; said molecular weight and concentration having values such that said aqueous solution is capable of providing wet coatings on said tissue.

5. A method of protecting from damage tissues or organs or parts thereof during harvesting thereof from animals or humans, subsequent manipulations and implantations of said tissues or organs or parts thereof in animals or humans, comprising providing said tissue and organ surfaces with a wet coating of a physiologically acceptable aqueous solution of a hydrophilic, polymeric material prior to and during said harvesting, manipulations and implantations thereof, wherein:

(a) said polymeric material is hyaluronic acid having a molecular weight from about 50,000 to less than about 500,000, a pharmaceutically acceptable salt thereof, complex thereof or mixtures thereof; and (b) the concentration in said aqueous solution of said polymeric material is in the range of from about 0.01% to about 15% by weight; said molecular weight and concentration having values such that said aqueous solution is capable of providing wet coatings on said tissue.

* * * * *